(12) United States Patent
Gao et al.

(10) Patent No.: US 12,429,423 B2
(45) Date of Patent: Sep. 30, 2025

(54) L-2-HYDROXYGLUTARATE BIOSENSOR BASED ON SPECIFIC TRANSCRIPTIONAL REGULATOR AND APPLICATION THEREOF

(71) Applicant: SHANDONG UNIVERSITY, Shandong (CN)

(72) Inventors: Chao Gao, Qingdao (CN); Zhaoqi Kang, Qingdao (CN); Cuiqing Ma, Qingdao (CN); Ping Xu, Qingdao (CN)

(73) Assignee: SHANDONG UNIVERSITY, Qingdao (CN)

( * ) Notice: Subject to any disclaimer, the term of this patent is extended or adjusted under 35 U.S.C. 154(b) by 770 days.

(21) Appl. No.: 17/626,801

(22) PCT Filed: Mar. 12, 2021

(86) PCT No.: PCT/CN2021/080524
§ 371 (c)(1),
(2) Date: Jan. 12, 2022

(87) PCT Pub. No.: WO2021/258784
PCT Pub. Date: Dec. 30, 2021

(65) Prior Publication Data
US 2022/0260496 A1    Aug. 18, 2022

(30) Foreign Application Priority Data

Jun. 23, 2020  (CN) .......................... 202010581540.9

(51) Int. Cl.
*C07K 14/21* (2006.01)
*C12N 15/70* (2006.01)
*C12N 15/85* (2006.01)
*G01N 21/64* (2006.01)

(52) U.S. Cl.
CPC ......... *G01N 21/6486* (2013.01); *C07K 14/21* (2013.01); *C12N 15/70* (2013.01); *C12N 15/85* (2013.01)

(58) Field of Classification Search
CPC ........ C12N 15/85; C12N 15/70; C07K 14/21; G01N 21/6486
See application file for complete search history.

(56) References Cited

FOREIGN PATENT DOCUMENTS

| CN | 104515852 A | 4/2015 |
| CN | 108303536 A | 7/2018 |
| CN | 111647056 A | 9/2020 |
| WO | 2013/127997 A1 | 9/2013 |

OTHER PUBLICATIONS

Vlad, Daniela, et al. "A modular steroid-inducible gene expression system for use in rice." BMC Plant Biology 19 (2019): 1-14. (Year: 2019).*
Xue, Ya-Ping, Cheng-Hao Cao, and Yu-Guo Zheng. "Enzymatic asymmetric synthesis of chiral amino acids." Chemical Society Reviews 47.4 (2018): 1516-1561. (Year: 2018).*
Bischof, Helmut et al., "Novel Genetically Encoded Fluorescent Probes Enable Real-Time Detection of Potassium in Vitro and in Vivo", Nature Communications, vol. 8, pp. 1-12.
Fernández-Galán, Esther et al., "Validation of a Routine Gas Chromatography Mass Spectrometry Method for 2-Hydroxyglutarate Quantification in Human Serum as a Screening Tool for Detection of IDH Mutations", Journal of Chromatography B 1083, (2018), pp. 28-34.
Kranendijk, Martijn et al., "Progress in Understanding 2-Hydroxyglutaric Acidurias", J Inherit Metab Dis, (2012), vol. 35, pp. 571-587.
Li, Hongde et al., "Drosophila Larvae Synthesize the Putative Oncometabolite L-2-Hydroxyglutarate During Normal Developmental Growth", PNAS, Feb. 7, 2017, vol. 114, No. 6, pp. 1353-1358.
Oldham, William M., et al., J., Hypoxia-Mediated Increases in L-2-Hydroxyglutarate Coordinate the Metabolic Response to Reductive Stress, Cell Metabolism, vol. 22, 14 pages, (2015).
Rzem, Rim et al., "A Gene Encoding a Putative Fad-Dependent L-2-Hydroxyglutarate Dehydrogenase is Mutated in L-2-Hydroxyglutaric Aciduria", PNAS, Nov. 30, 2004, vol. 101, No. 48, pp. 16849-16854.
Shelar, Sandeep Balu et al., "Biochemical and Epigenetic Insights Into L-2 Hydroxyglutarate, a Potential Therapeutic Target in Renal Cancer", American Association for Cancer Research, (2018), pp. 1-49.
Shim, Eun-Hee et al., "L-2-Hydroxyglutarate: an Epigenetic Modifier and Putative Oncometabolite in Renal Cancer", American Association for Cancer, Sep. 2, 2014, pp. 1-27.
Struys, Eduard A. et al., "Measurement of Urinary D- and L-2-Hydroxyglutarate Enantiomers by Stable-Isotope Dilution Liquid Chromatography-Tandem Mass Spectrometry After Derivatization With Diacetyl-L-Tartaric Anhydride", Clinical Chemistry, vol. 50, No. 8 (2004), pp. 1391-1395.
Tyrakis, Petros A. et al., "S-2-Hydroxyglutarate Regulates CD8+ T-Lymphocyte Fate", Nature, (2016), pp. 1-23.

(Continued)

*Primary Examiner* — Robert J Yamasaki
*Assistant Examiner* — Trevor Kane
(74) *Attorney, Agent, or Firm* — Oliff PLC (57) ABSTRACT

A transcriptional regulator LhgR is specifically responsive to L-2-hydroxyglutarate (L-2-HG) and an L-2-HG biosensor based on this transcriptional regulator; wherein the biosensor is a fusion protein of cyan fluorescent protein mTFP, L-2-HG specific transcriptional regulator LhgR, and yellow fluorescent protein Venus, including three types of L-2-HG biosensor $LHGFR_{0N0C}$, $LHGFR_{0N3C}$, and $LHGFR_{0N7C}$. The application of the L-2-HG biosensor in the detection of L-2-HG-containing biological samples, real-time detection of intracellular L-2-HG concentration in bacteria and in human cells. The experiments confirmed that the biosensor can achieve high specificity, sensitivity, and accuracy in the detection of L-2-HG and can determine intracellular L-2-HG dynamics in real time, which has good application prospects.

5 Claims, 6 Drawing Sheets

Specification includes a Sequence Listing.

(56) References Cited

OTHER PUBLICATIONS

Xu, Wei et al., "Oncometabolite 2-Hydroxyglutarate is a Competitive Inhibitor Of α-Ketoglutarate-Dependent Dioxygenases", Cancer Cell, vol. 19, Jan. 18, 2011, pp. 17-30.
Zhang, Manman et al., "Increased Glutarate Production By Blocking the Glutaryl-Coa Dehydrogenation Pathway and a Catabolic Pathway Involving L-2-Hydroxyglutarate", Nature Communications, vol. 9, (2018), pp. 1-14.
Zhang, William H. et al., "Monitoring Hippocampal Glycine With the Computationally Designed Optical Sensor GlyFS", Nature Chemical Biology, (2017), pp. 1-13.
Kang, Zhaoqi et al., "A Fluorescent L-2-Hydroxyglutarate Biosensor", 47 pages.
Kang, Zhaoqi et al., "An L-2-Hydroxyglutarate Biosensor Based on Specific Transcriptional Regulator LhgR", Nature Communications, (2021), pp. 1-13.
Chen, Yan-hong et al., "Oncometabolite 2-HG in Glioma Evolution and Recent Progress of Detection Method", Chinese Pharmacological Bulletin, (2018), vol. 34, No. 7, pp. 898-902.
Pseudomonas Putida W619 Chromosome, Complete Genome, COVID-19 Information, pp. 1-2.
Jul. 5, 2021 Office Action issued in Chinese Patent Application No. 202010581540.9.
Jun. 3, 2021 Search Report issued in International Patent Application No. PCT/CN2021/080524.
Jun. 3, 2021 Written Opinion issued in International Patent Application No. PCT/CN2021/080524.
Multispecies: FadR Family Transcriptional Regulator [Pseudomonas], Covid-19 Information, pp. 1.

\* cited by examiner

SEQUENCE LISTING

<160> NUMBER OF SEQ ID NOS: 4

<210> SEQ ID NO 1
<211> LENGTH: 711
<212> TYPE: DNA
<213> ORGANISM: Artificial sequence
<220> FEATURE:
<223> OTHER INFORMATION: Nucleotide sequence of LhgR, a transcriptional
      regulator of the L-2-hydroxyglutarate acid

<400> SEQUENCE: 1

```
atgctagaac tccagcgccc cgacactctg gtcgaacggg ttgtcagcgc catccgtgca      60
gaaatcgatt ccggtcgcct ggccgccgaa gcgcgcctgc ccactgaaca gcaactggct     120
gaacaactga acgtcagccg ctcggtagtg cgcgaagcgg tagcgcagct caaggccgat     180
ggcgtgctga tcgcccgccg cgggcttggc tcctatatct cgaaaacccc cgggggcacg     240
gtgttccgct tccccggcag taccggtcgc aaacccgacc tggtgcagat gttcgaaatg     300
cgcctgtgga tcgaaaccca ggcagcggcc atcgccgcgc gccgacgtga cgaacacgat     360
ctggcgaaca tgcccaggc cctgcaggag atgctcgaca aacgcagcga cttcgccact     420
gcctcggcag ctgatgtggc cttccacagg gccatcgccg aagccagcaa gaacgattac     480
```

```
ttcgtggcct tccatgactt tctcggcggc cagttggcca atgcacggcg caccgcctgg      540
gaaaactccg cagcccattc ggtgggcggc tcggccgaag ccaatcgcga acaccaagcg      600
ctttatcagg ccatcgccga cggtgaccgc caaagggctg cggcgtgtgc cgaagcgcat      660
ctgcgcgcct ctgccaaacg cctgaaaata gaactacctg cactcgactg a              711
```

<210> SEQ ID NO 2
<211> LENGTH: 2148
<212> TYPE: DNA
<213> ORGANISM: Artificial sequence
<220> FEATURE:
<223> OTHER INFORMATION: Nucleotide sequence of the L-2-HG biosensor
      LHGFR0N0C

<400> SEQUENCE: 2

```
atggtgagca agggcgagga gaccacaatg ggcgtaatca agcccgacat gaagatcaag       60
ctgaagatgg agggcaacgt gaatggccac gccttcgtga tcgagggcga gggcgagggc      120
aagcctacgc acggcaccaa caccatcaac ctggaggtga aggagggagc ccccctgccc      180
ttctcctacg acattctgac caccgcgttc gcctacggca cagggccttt caccaagtac      240
cccgacgaca tccccaacta cttcaagcag tccttccccg agggctactc ttgggagcgc      300
accatgacct tcgaggacaa gggcatcgtg aaggtgaagt ccgacatctc catggaggag      360
gactccttca tctacgagat acacctcaag ggcgagaact tccccccaa cggccccgtg       420 atgcagaaga gaccaccgg ctgggacgcc tccaccgaga ggatgtacgt gcgcgacggc       480
gtgctgaagg gcgacgtcaa gcacaagctg ctgctggagg cggcggcca ccaccgcgtt       540 gacttcaaga ccatctacag ggccaagaag gcggtgaagc tgcccgacta tcactttgtg      600
gaccaccgca tcgagatcct gaaccacgac aaggactaca acaaggtgac cgtttacgag      660
agcgccgtgg cccgcaactc caccgacggc atggacgagc tgtacaagga gctcatgcta      720
gaactccagc gccccgacac tctggtcgaa cgggttgtca cgccatccg tgcagaaatc       780 gattccggtc gcctggccgc cgaagcgcgc ctgcccactg aacagcaact ggctgaacaa      840
ctgaacgtca gccgctcggt agtgcgcgaa gcggtagcgc agctcaaggc cgatggcgtg      900
ctgatcgccc gccgcgggct tggctcctat atctcgaaaa ccccccggggg cacggtgttc      960 cgcttccccg gcagtaccgg tcgcaaaccc gacctggtgc agatgttcga aatgcgcctg     1020
tggatcgaaa cccaggcagc ggccatcgcc gcgcgccgac gtgacgaaca cgatctggcg     1080
aacatggccc aggccctgca ggagatgctc gacaaacgca gcgacttcgc cactgcctcg     1140
gcagctgatg tggccttcca cagggccatc gccgaagcca gcaagaacga ttacttcgtg     1200
gccttccatg actttctcgg cggccagttg gccaatgcac ggcgcaccgc ctgggaaaac     1260
tccgcagccc attcggtggg cggctcggcc gaagccaatc gcaacaccaa gcgctttat     1320 caggccatcg ccgacggtga ccgccaaagg gctgcggcgt gtgccgaagc gcatctgcgc     1380
gcctctgcca aacgcctgaa aatagaacta cctgcactcg acgtcgacat ggtgagtaaa     1440
ggcgaagaac tgtttaccgg cgttgttccg attctggttg aactggatgg cgatgttaat     1500
ggccataaat ttctgtgag cggcgaaggc gaaggtgacg ctacatatgg caaactgacc     1560
ctgaaactga tttgtaccac cggtaaactg ccggtgccgt ggcctacact ggtgacaaca     1620
ctgggttatg gcctgcagtg ctttgcccgt tatccggatc atatgaaaca gcatgatttc     1680
tttaagagcg caatgccgga aggttatgtt caggaacgca ccattttctt taaagatgat     1740
ggcaattaca agacccgtgc agaagttaaa tttgaaggcg ataccctggt taatcgtatt     1800
```

```
gaactgaaag gcattgattt taaagaggat ggcaatattc tgggtcataa actggaatat    1860
aactataata gccacaacgt gtatatcacc gcagataaac agaaaaatgg tattaaggcc    1920
aatttcaaaa tccgccataa tattgaagac ggcggcgtgc agctggcaga tcattatcag    1980
cagaataccc cgattggtga cggtccggtg ctgttaccgg ataatcatta tctgagttat    2040
cagagcgcac tgagtaaaga tccgaatgaa aaacgtgatc atatggtgct gctggaattt    2100
gtgaccgccg caggtattac cctgggcatg gatgaactgt ataaataa                 2148
```

<210> SEQ ID NO 3
<211> LENGTH: 2139
<212> TYPE: DNA
<213> ORGANISM: Artificial sequence
<220> FEATURE:
<223> OTHER INFORMATION: Nucleotide sequence of the L-2-HG biosensor
      LHGFR0N3C

<400> SEQUENCE: 3

```
atggtgagca agggcgagga gaccacaatg ggcgtaatca gcccgacat gaagatcaag      60 ctgaagatgg agggcaacgt gaatggccac gccttcgtga tcgagggcga gggcgagggc    120
aagccctacg acggcaccaa caccatcaac ctggaggtga aggagggagc cccctgccc     180 ttctcctacg acattctgac caccgcgttc gcctacggca cagggcctt caccaagtac    240 cccgacgaca tccccaacta cttcaagcag tccttccccg agggctactc ttgggagcgc    300
accatgacct tcgaggacaa gggcatcgtg aaggtgaagt ccgacatctc catggaggag    360
gactccttca tctacgagat acacctcaag ggcgagaact ccccccccaa cggccccgtg    420
atgcagaaga agaccaccgg ctgggacgcc tccaccgaga ggatgtacgt gcgcgacggc    480
gtgctgaagg gcgacgtcaa gcacaagctg ctgctggagg cggcggcca ccaccgcgtt    540 gacttcaaga ccatctacag ggccaagaag gcggtgaagc tgcccgacta tcactttgtg    600
gaccaccgca tcgagatcct gaaccacgac aaggactaca acaaggtgac cgtttacgag    660
agcgccgtgg cccgcaactc caccgacggc atggacgagc tgtacaagga gctcatgcta    720
gaactccagc gccccgacac tctggtcgaa cgggttgtca cgccatccg tgcagaaatc    780 gattccggtc gcctggccgc cgaagcgcgc ctgcccactg aacagcaact ggctgaacaa    840
ctgaacgtca gccgctcggt agtgcgcgaa gcggtagcgc agctcaaggc cgatggcgtg    900
ctgatcgccc gccgcgggct tggctcctat atctcgaaaa ccccgggggg cacggtgttc    960
cgcttccccg gcagtaccgg tcgcaaaccc gacctggtgc agatgttcga atgcgcctg   1020 tggatcgaaa cccaggcagc ggccatcgcc gcgcgccgac gtgacgaaca cgatctggcg   1080
aacatggccc aggccctgca ggagatgctc gacaaacgca gcgacttcgc cactgcctcg   1140
gcagctgatg tggccttcca cagggccatc gccgaagcca gcaagaacga ttacttcgtg   1200
gccttccatg actttctcgg cggccagttg gccaatgcac ggcgcaccgc ctgggaaaac   1260
tccgcagccc attcggtggg cggctcggcc gaagccaatc gcgaacacca gcgctttat    1320 caggccatcg ccgacggtga ccgccaaagg gctgcggcgt gtgccgaagc gcatctgcgc   1380
gcctctgcca aacgcctgaa aatagaacta cctgtcgaca tggtgagtaa aggcgaagaa   1440
ctgtttaccg gcgttgttcc gattctggtt gaactggatg gcgatgttaa tggccataaa   1500
ttttctgtga gcggcgaagg cgaaggtgac gctacatatg gcaaactgac cctgaaactg   1560
atttgtacca ccggtaaact gccggtgccg tggcctacac tggtgacaac actgggttat   1620
ggcctgcagt gctttgcccg ttatccggat catatgaaac agcatgattt ctttaagagc   1680
```

| | |
|---|---|
| gcaatgccgg aaggttatgt tcaggaacgc accatttttct ttaaagatga tggcaattac | 1740 |
| aagacccgtg cagaagttaa atttgaaggc gataccctgg ttaatcgtat tgaactgaaa | 1800 |
| ggcattgatt ttaaagagga tggcaatatt ctgggtcata aactggaata taactataat | 1860 |
| agccacaacg tgtatatcac cgcagataaa cagaaaaatg gtattaaggc caatttcaaa | 1920 |
| atccgccata atattgaaga cggcggcgtg cagctggcag atcattatca gcagaatacc | 1980 |
| ccgattggtg acggtccggt gctgttaccg gataatcatt atctgagtta tcagagcgca | 2040 |
| ctgagtaaag atccgaatga aaaacgtgat catatggtgc tgctggaatt tgtgaccgcc | 2100 |
| gcaggtatta ccctgggcat ggatgaactg tataaataa | 2139 |

<210> SEQ ID NO 4
<211> LENGTH: 2127
<212> TYPE: DNA
<213> ORGANISM: Artificial sequence
<220> FEATURE:
<223> OTHER INFORMATION: Nucleotide sequence of the L-2-HG biosensor
      LHGFR0N7C

<400> SEQUENCE: 4

| | |
|---|---|
| atggtgagca agggcgagga gaccacaatg ggcgtaatca gcccgacat gaagatcaag | 60 |
| ctgaagatgg agggcaacgt gaatggccac gccttcgtga tcgagggcga gggcgagggc | 120 |
| aagccctacg acgcaccaa caccatcaac ctggaggtga aggagggagc cccctgccc | 180 |
| ttctcctacg acattctgac caccgcgttc gcctacggca cagggccttt caccaagtac | 240 |
| cccgacgaca tccccaacta cttcaagcag tccttccccg agggctactc ttgggagcgc | 300 |
| accatgacct tcgaggacaa gggcatcgtg aaggtgaagt ccgacatctc catggaggag | 360 |
| gactccttca tctacgagat acacctcaag ggcgagaact ccccccccaa cggccccgtg | 420 |
| atgcagaaga agaccaccgg ctgggacgcc tccaccgaga ggatgtacgt gcgcgacggc | 480 |
| gtgctgaagg gcgacgtcaa gcacaagctg ctgctggagg gcggcggcca ccaccgcgtt | 540 |
| gacttcaaga ccatctacag ggccaagaag gcggtgaagc tgcccgacta tcactttgtg | 600 |
| gaccaccgca tcgagatcct gaaccacgac aaggactaca acaaggtgac cgtttacgag | 660 |
| agcgccgtgg cccgcaactc caccgacggc atggacgagc tgtacaagga gctcatgcta | 720 |
| gaactccagc gccccgacac tctggtcgaa cgggttgtca gcgccatccg tgcagaaatc | 780 |
| gattccggtc gcctggccgc cgaagcgcgc ctgcccactg aacagcaact ggctgaacaa | 840 |
| ctgaacgtca gccgctcggt agtgcgcgaa gcggtagcgc agctcaaggc cgatggcgtg | 900 |
| ctgatcgccc gccgcgggct tggctcctat atctcgaaaa ccccgggggg cacggtgttc | 960 |
| cgcttccccg gcagtaccgg tcgcaaaccc gacctggtgc agatgttcga aatgcgcctg | 1020 |
| tggatcgaaa cccaggcagc ggccatcgcc gcgcgccgac gtgacgaaca cgatctggcg | 1080 |
| aacatggccc aggccctgca ggagatgctc gacaaacgca gcgacttcgc cactgcctcg | 1140 |
| gcagctgatg tggccttcca cagggccatc gccgaagcca gcaagaacga ttacttcgtg | 1200 |
| gccttccatg actttctcgg cggccagttg gccaatgcac ggcgcaccgc ctgggaaaac | 1260 |
| tccgcagccc attcggtggg cggctcggcc gaagccaatc gcgaacacca agcgctttat | 1320 |
| caggccatcg ccgacggtga ccgccaaagg gctgcgcgcgt gtgccgaagc gcatctgcgc | 1380 |
| gcctctgcca aacgcctgaa agtcgacatg gtgagtaaag gcgaagaact gtttaccggc | 1440 |
| gttgttccga ttctggttga actggatggc gatgttaatg gccataaatt ttctgtgagc | 1500 |
| ggcgaaggcg aaggtgacgc tacatatggc aaactgaccc tgaaactgat ttgtaccacc | 1560 |

```
ggtaaactgc cggtgccgtg gcctacactg gtgacaacac tgggttatgg cctgcagtgc    1620
tttgcccgtt atccggatca tatgaaacag catgatttct ttaagagcgc aatgccggaa    1680
ggttatgttc aggaacgcac cattttcttt aaagatgatg gcaattacaa gacccgtgca    1740
gaagttaaat ttgaaggcga taccctggtt aatcgtattg aactgaaagg cattgatttt    1800
aaagaggatg gcaatattct gggtcataaa ctggaatata actataatag ccacaacgtg    1860
tatatcaccg cagataaaca gaaaaatggt attaaggcca atttcaaaat ccgccataat    1920
attgaagacg gcggcgtgca gctggcagat cattatcagc agaataccccc gattggtgac    1980 ggtccggtgc tgttaccgga taatcattat ctgagttatc agagcgcact gagtaaagat    2040
ccgaatgaaa aacgtgatca tatggtgctg ctggaatttg tgaccgccgc aggtattacc    2100
ctgggcatgg atgaactgta taaataa                                        2127
```

L-2-HYDROXYGLUTARATE BIOSENSOR BASED ON SPECIFIC TRANSCRIPTIONAL REGULATOR AND APPLICATION THEREOF

CROSS-REFERENCES TO RELATED APPLICATIONS

This application claims priority benefits to Chinese Patent Application No. 202010581540.9, filed 23 Jun. 2020, the contents of which are incorporated herein by reference.

TECHNICAL FIELD

The present application relates to a biosensor and application thereof, especially to L-2-hydroxyglutarate biosensor based on specific transcriptional regulator and application thereof, which belongs to the field of genetic engineering technology.

BACKGROUND

The information disclosed in the background is intended to increase the understanding of the overall background of the application, and the disclosure should not necessarily be regarded as an acknowledgement or in any form implying that the information has become prior art known to those of ordinary skill in the art.

L-2-Hydroxyglutarate (L-2-HG) is involved in numerous physiological processes in life and is produced in mammals and plants by the reduction of 2-ketoglutarate by lactate dehydrogenase LDH and malate dehydrogenase MDH under hypoxic conditions[1], and as an important metabolic intermediate of glutarate hydroxylation pathway mediated by glutarate hydroxylase CsiD in microorganisms[2]. L-2-HG dehydrogenase (L2HGDH) or L-2-HG oxidase (LhgO), that converts L-2-HG to 2-KG, plays an indispensable role in the catabolism of L-2-HG[3]. However, the regulatory mechanism of L-2-HG metabolism has not been elucidated. L-2-HG is considered as a marker of several cancers[4] and is able to inhibit the activity of several 2-ketoglutarate-dependent dioxygenases[5], whose accumulation leads to cancer, L-2-hydroxyglutaric aciduria[6, 7]. In addition, L-2-HG can promote the proliferation and antitumor capacity of CD8+ T lymphocytes[8], relieve the cellular reductive stress[1], and coordinate glycolytic fluxes[9]. Given the diversity and complexity of the physiological functions of L-2-HG in cellular metabolism, the establishment of a real-time detection method for intracellular L-2-HG is of great significance and vital importance.

The reported L-2-HG detection methods include LC-MS/MS and GC-MS/MS[10, 11], which are not only time-consuming, cumbersome, and lacking in spatial and temporal resolution, limiting the development of L-2-HG-related diagnostic techniques. Several small molecule biosensors based on Forster Resonance Energy Transfer (FRET) technology have been developed and widely used to determine the intracellular dynamics of metabolites[12, 13], which consists of a recognition element that specifically binds to a ligand and a pair of fluorescent proteins that induce conformational changes upon ligand binding, which in turn affects the optical properties of the biosensor (changes in the emission ratio between fluorescent proteins can reflect changes in the concentration of the ligand). The basis for the construction of biosensors based on FRET technology is the screening to obtain recognition elements that specifically respond to the ligand, and the screening based on specific transcriptional regulators responding to L-2-HG helps to develop L-2-HG biosensors based on FRET technology. After searching, there are no reports about L-2-HG-specific transcriptional regulators, L-2-HG biosensors based on specific transcriptional regulators, and methods for applying the biosensors to detect L-2-HG-containing biological samples or to detect intracellular L-2-HG concentrations in bacteria and human cells in real time.

REFERENCES

[1] Oldham, W. M., Clish, C. B., Yang, Y. & Loscalzo, J. Hypoxia-mediated increases in L-2-hydroxyglutarate coordinate the metabolic response to reductive stress. *Cell Metab.* 22, 291-303 (2015).
[2] Zhang, M. et al. Increased glutarate production by blocking the glutaryl-CoA dehydrogenation pathway and a catabolic pathway involving L-2-hydroxyglutarate. *Nat. Commun.* 9, 2114 (2018).
[3] Rzem, R. et al. A gene encoding a putative FAD-dependent L-2-hydroxyglutarate dehydrogenase is mutated in L-2-hydroxyglutaric aciduria. *Proc. Natl. Acad. Sci. USA* 101, 16849-16854 (2004).
[4] Shelar, S. et al. Biochemical and epigenetic insights into L-2-hydroxyglutarate, a potential therapeutic target in renal cancer. *Clin. Cancer Res.* 24, 6433-6446 (2018).
[5] Xu, W. et al. Oncometabolite 2-hydroxyglutarate is a competitive inhibitor of α-ketoglutarate-dependent dioxygenases. *Cancer Cell* 19, 17-30 (2011). [6] Shim, E. H. et al. L-2-Hydroxyglutarate: an epigenetic modifier and putative oncometabolite in renal cancer. *Cancer Discov.* 4, 1290-1298 (2014).
[7] Kranendijk, M., Struys, E. A., Salomons, G. S., Van der Knaap, M. S. & Jakobs, C. Progress in understanding 2-hydroxyglutaric acidurias. *J. Inherit. Metab. Dis.* 35, 571-587 (2012).
[8] Tyrakis, P. A. et al. S-2-hydroxyglutarate regulates CD8+ T-lymphocyte fate. *Nature* 540, 236-241 (2016).
[9] Li, H. et al. Drosophila larvae synthesize the putative oncometabolite L-2-hydroxyglutarate during normal developmental growth. *Proc. Natl. Acad. Sci. USA* 114, 1353-1358 (2017).
[10] Struys, E. A., Jansen, E. E., Verhoeven, N. M. & Jakobs, C. Measurement of urinary D- and L-2-hydroxyglutarate enantiomers by stable-isotopedilution liquid chromatography-tandem mass spectrometry after derivatization with diacetyl-L-tartaric anhydride. *Clin. Chem.* 50, 1391-1395 (2004).
[11] Fernandez-Galan, E. et al. Validation of a routine gas chromatography mass spectrometry method for 2-hydroxyglutarate quantification in human serum as a screening tool for detection of idh mutations. *J. Chromatogr. B. Analyt. Technol. Biomed. Life. Sci.* 1083, 28-34 (2018).
[12] Bischof, H. et al. Novel genetically encoded fluorescent probes enable real-time detection of potassium in vitro and in vivo. *Nat. Commun.* 8, 1422 (2017).
[13] Zhang, W. H. et al. Monitoring hippocampal glycine with the computationally designed optical sensor GlyFS. *Nat. Chem. Biol.* 14, 861-869 (2018).

SUMMARY

In response to the shortcomings of the L-2-HG detection methods in prior art that are time-consuming, cumbersome, and difficult to meet the intracellular real-time monitoring, the present application provides an L-2-hydroxyglutarate (L-2-HG) biosensor based on the specific transcriptional regulator LhgR and applications thereof. The biosensor is based on the L-2-HG specific transcriptional regulator LhgR, coupled with Forster Resonance Energy Transfer (FRET) technology to achieve fast, sensitive, and accurate detection of L-2-HG concentration and output with fluorescence signal, and can measure the dynamic changes of intracellular L-2-HG concentration in real time.

The transcriptional regulator specifically responsive to L-2-hydroxyglutarate (L-2-HG) as described in the present application, named LhgR, wherein, the transcriptional regulator LhgR is derived from *Pseudomonas putida* W619 and belongs to the transcriptional repressor proteins of GntR family, which is located upstream of the gene encoding L-2-hydroxyglutarate oxidase LhgO in the genome, capable of binding to the promoter region of lhgO, regulating L-2-HG catabolism, and specifically responding to L-2-HG; the nucleotide sequence of the transcriptional regulator LhgR is shown in SEQ ID NO. 1.

The above transcriptional regulator that specifically responds to L-2-hydroxyglutarate (L-2-HG) was obtained in the following way:
(1) analysis of the distribution of lhgO, the gene encoding a key enzyme for L-2-HG catabolism, in the genomes of different strains. A gene encoding a GntR family transcriptional regulator, lhgR, was found directly upstream of lhgO in the genome of *Pseudomonas putida* W619. lhgR gene was synthesized and cloned into pETDuet-1 vector, and the recombinant plasmid pETDuet-lhgR was introduced into an expression strain *Escherichia coli* BL21 (DE3), and then LhgR protein was obtained by induction of expression, isolation, and purification;
(2) electrophoretic mobility shift assays were performed to verify and determine the function of the above transcriptional regulator LhgR in *Pseudomonas putida* W619. Purified LhgR was incubated with different compounds (L-lysine, 5-aminovalerate, glutarate, D-2-HG, 2-ketoglutarate, and succinate), respectively, then the promoter fragment of lhgO was added. The effect on the binding ability of LhgR to the lhgO promoter fragment in the presence of different compounds was analyzed by electrophoretic separation, staining, and imaging. The experiments showed that only L-2-HG inhibited the binding of LhgR to the lhgO promoter fragment, demonstrating that LhgR is a transcriptional regulator that specifically responds to L-2-HG.

The L-2-hydroxyglutarate (L-2-HG) biosensor based on specific transcriptional regulators as described in the present application, wherein the biosensor is a fusion protein of cyan fluorescent protein mTFP, L-2-HG specific transcriptional regulator LhgR, and yellow fluorescent protein Venus; it includes three types of L-2-HG biosensor $LHGFR_{ON0C}$, $LHGFR_{ON3C}$, and $LHGFR_{ON7C}$, wherein the nucleotide sequences of $LHGFR_{ON0C}$, $LHGFR_{ON3C}$, and $LHGFR_{ON7C}$ are shown in SEQ ID NO. 2, SEQ ID NO. 3, and SEQ ID NO. 4, respectively; the binding of L-2-HG to the biosensor induces the conformational change of the biosensor, resulting in a change in the ratio of emission intensity between fluorescent proteins, accompanied by an increase in the concentration of L-2-HG, the ratio of emission intensity of the biosensor also increases, which can be used as an indicator to achieve specific detection of L-2-HG; wherein the response of biosensor for L-2-HG is determined by introducing the sensor-encoding plasmid into the expression strain *E. coli* BL21 (DE3), inducing expression, isolating and purifying, diluting to 1 μM using 50 mM pH 7.4 Tris-HCl, mixing with gradient concentrations of L-2-HG in a 3:1 volume ratio, and measuring the emission ratio by using a fluorescence microplate reader with excitation at 430 nm, emission at 485 nm and 528 nm.

The above method for the construction of L-2-hydroxyglutarate biosensor based on specific transcriptional regulators comprises the following steps:
(1) cyan fluorescent protein mTFP encoding gene and yellow fluorescent protein Venus encoding gene were synthesized, PCR amplified, and cloned into pETDuet-1 vector using the BamHI and SacI restriction sites, and SalI and NotI restriction sites, respectively, to obtain recombinant plasmid pETDuet-mTFP-Venus;
(2) transcriptional regulator LhgR in *Pseudomonas putida* W619 was synthesized, PCR amplified, and cloned into the recombinant plasmid pETDuet-mTFP-Venus using SacI/SalI restriction sites to obtain recombinant plasmid pETDuet-$LHGFR_{ON0C}$, which was named L-2-HG biosensor $LHGFR_{ON0C}$;
(3) to improve the sensitivity of the biosensor for L-2-HG detection, the N-terminal and C-terminal amino acids of the L-2-HG-specific transcriptional regulator LhgR were truncated to optimize the biosensor: the truncated variant of LhgR was amplified by PCR, i.e., the combination of the N-terminal and C-terminal truncated amino acids of LhgR, and the obtained truncated fragment was inserted into pETDuet-mTFP-Venus using SacI/SalI restriction sites, and after construction and screening, a recombinant plasmid pETDuet-$LHGFR_{ON3C}$ with a C-terminal truncation of three amino acids of LhgR was obtained, which was named L-2-HG biosensor $LHGFR_{ON3C}$, or a recombinant plasmid pETDuet-$LHGFR_{ON7C}$ with a C-terminal truncation of seven amino acids of LhgR was obtained, which was named L-2-HG biosensor $LHGFR_{ON7C}$.

Application of L-2-hydroxyglutarate biosensor based on specific transcriptional regulators as described in the present application in the detection of L-2-HG-containing biological samples.

The above application is performed by preparing a gradient solution of L-2-HG using serum, urine of a healthy adult or bacterial culture medium, mixing with purified L-2-HG biosensor in volume ratio of 1:3 under light-proof conditions, and measuring the fluorescence emission intensities of mTFP and Venus using a fluorescence microplate reader, subtracting the background fluorescence intensity without L-2-HG biosensor at each emission wavelength. Dose-response curves and quantitative results for L-2-HG in various biological samples were obtained; wherein the L-2-HG biosensor exhibited a dose-dependent increase in the ratio of fluorescence emission intensity in response to an increase in the concentration of L-2-HG in serum, urine, or bacterial culture medium, and the results of this biosensor for the determination of L-2-HG in biological samples were consistent with those of liquid chromatography-mass spectrometry (LC-MS/MS), indicating the accuracy of the biosensor in the quantitative determination of L-2-HG.

Application of L-2-hydroxyglutarate biosensor based on specific transcriptional regulator as described in the present application in real-time detection of bacterial intracellular L-2-HG concentration.

The above application was performed by introducing the L-2-HG biosensor-encoding plasmid pETDuet-$LHGFR_{ON3C}$ into an expression strain *E. coli* BL21 (DE3), shaking the culture and then adding IPTG overnight to induce $LHGFR_{ON3C}$ expression, carbon starvation treatment in inorganic salt medium without carbon source for 8 h to remove intracellular L-2-HG, mixing 90 μL of carbon starvation-treated bacterial solution with 10 μL of gradient concentration of L-2-HG solution, the fluorescence emission intensity of mTFP and Venus and its ratio were measured continuously at 5-minute intervals by a fluorescence microplate reader, and the fluorescence emission ratio increased in response to the addition of L-2-HG, and there was a positive correlation between the change level of fluorescence emission ratio and the concentration of L-2-HG, which can be used as an indicator to achieve real-time detection of dynamic changes in intracellular L-2-HG concentration of bacteria.

Application of L-2-hydroxyglutarate biosensor based on specific transcriptional regulator as described in the present application in the detection of intracellular L-2-HG concentration in human cells.

The above application was performed by optimizing and synthesizing the nucleotide sequences of $LHGFR_{ON3C}$ and $LHGFR_{ON7C}$ with mammalian codons, adding the kozark sequence, 5'-GCCACC-3', before the start codon, and ligating it to the pcDNA3.1$^{(+)}$ plasmid, then the obtained recombinant plasmids pcDNA3.1-$LHGFR_{ON3C}$ and pcDNA3.1-$LHGFR_{ON7C}$ were transfected into HEK293FT cells, respectively. Cells were trypsinized 48 h following transfection, and resuspended in 1× Hank's balanced salt solution supplemented with 20 mM HEPES. Digitonin at a concentration of 10 μM was used to induce cell permeabilization and deplete intracellular L-2-HG for in vivo response curves construction. 90 μL of the treated cell suspension was mixed with 10 μL of gradient concentrations of L-2-HG, and the fluorescence emission intensities of mTFP and Venus were measured by using a fluorescence microplate reader, where $LHGFR_{ON3C}$ and $LHGFR_{ON7C}$ were able to detect intracellular L-2-HG concentration in human cells, and the fluorescence emission ratio of the L-2-HG biosensor increased in response to the addition of L-2-HG.

The substantial features and outstanding effects of the present application are as follows:

(1) based on neighborhood analysis of lhgO, a gene encoding a key enzyme for L-2-HG catabolism, in the genomes of different strains, combined with electrophoretic mobility shift assays, the present application identifies the first transcriptional regulator LhgR in *Pseudomonas putida* W619 that regulates L-2-HG catabolism and specifically responds to L-2-HG;

(2) based on the characteristics of conformational change after binding of transcriptional regulator LhgR and L-2-HG, coupled with Forster Resonance Energy Transfer technology, the present application constructs L-2-HG biosensor LHGFR by inserting LhgR between cyan fluorescent protein mTFP and yellow fluorescent protein Venus, which can convert L-2-HG concentration signal into fluorescence intensity signal output, and it has strong specificity to L-2-HG and can achieve rapid and sensitive detection of L-2-HG;

(3) the L-2-HG biosensor constructed by the present application has similar quantification results to the conventional detection method LC-MS/MS for the quantification of L-2-HG in various biological samples including serum, urine, and bacterial culture medium, indicating that the method has good accuracy and has good prospects for clinical application in the rapid diagnosis and treatment of L-2-HG-related diseases;

(4) the L-2-HG biosensor constructed by the present application can be expressed in cells, combined with a fluorescent microplate reader can detect intracellular L-2-HG dynamics in real time, which is expected to elucidate the physiological and pathological functions of L-2-HG in human cells.

BRIEF DESCRIPTION OF THE DRAWINGS

The accompanying drawings, which are incorporated in and constitute a part of this application, are included to provide a further understanding of the application, and the description of the exemplary embodiments and illustrations of the application are intended to explain the application and are not intended to limit the application.

DETAILED DESCRIPTION

The following is a detailed description of the contents of the present application in conjunction with the specific accompanying drawings and examples. It should be noted that the following description is intended only to explain the invention, not to limit it in any way, and that any simple modifications, equivalent changes and modifications to the embodiment based on the technical substance of the invention are within the scope of the technical solution of the invention.

In the following examples, the experimental methods used, which are not specifically described, are conventional methods. The strains, cells, materials, and reagents used were obtained from commercial sources, if not otherwise specified.

Example 1: Acquisition and Characterization of LhgR, a Transcriptional Regulator of L-2-hydroxyglutarate (L-2-HG)

(1) Expression and Purification of LhgR

Figure 1:
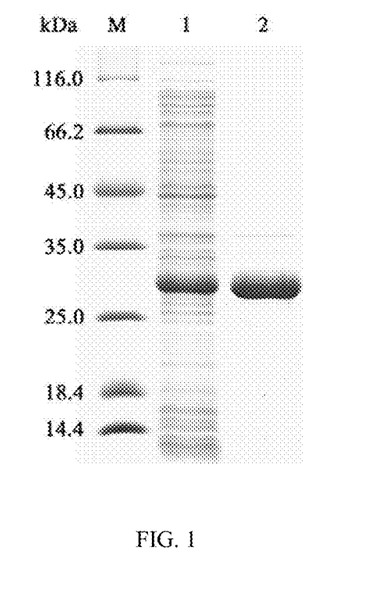
FIG. 1: SDS-PAGE analysis of LhgR.

Gene fragments derived from *Pseudomonas putida* W619 containing lhgR promoter (F2), lhgR gene, lhgO promoter (F1), and lhgO gene (see NCBI database ncbi.nlm.nih.gov/, accession number NC_010501.1) were synthesized by General Biosystem Co., Ltd (Anhui), ligated in pETDuet-1 plasmid, and preserved in *Escherichia coli* Top10 strain. The recombinant plasmid pETDuet-F2-lhgR-F1-lhgO was extracted from this strain, the lhgR gene was amplified by PCR using the synthetic primers, and a recombinant plasmid pETDuet-lhgR was obtained by double digestion of the gene fragment with the pETDuet-1 plasmid using BamHI/HindIII and ligation by T4 DNA ligase, which was transformed into an expression strain E. coli BL21 (DE3), and coated on LB plates containing ampicillin resistance to screen the successful strains. Single colonies were picked, verified by PCR, inoculated in 1 L of LB medium containing ampicillin resistance, and incubated at 37° C. with 180 rpm to an $OD_{600\,nm}$ of approximately 0.6. Then, 1 mM IPTG was added, and LhgR expression was induced overnight at 16° C. with 160 rpm, followed by protein isolation and purification. The purification results are shown in FIG. 1; the sequence length of the lhgR gene is 711 bases, and its nucleotide sequence is shown in SEQ ID NO. 1.

The lhgR gene of *Pseudomonas putida* W619 was amplified by PCR with the following primer design.

```
Upstream primer:
5'-AATTGGATCCGATGCTAGAACTCCAGC-3',
carrying a BamHI site.

Downstream primer:
5'-AATTAAGCTTTCAGTCGAGTGCAGGT-3',
carrying a HindIII site.
```

Figure 2:
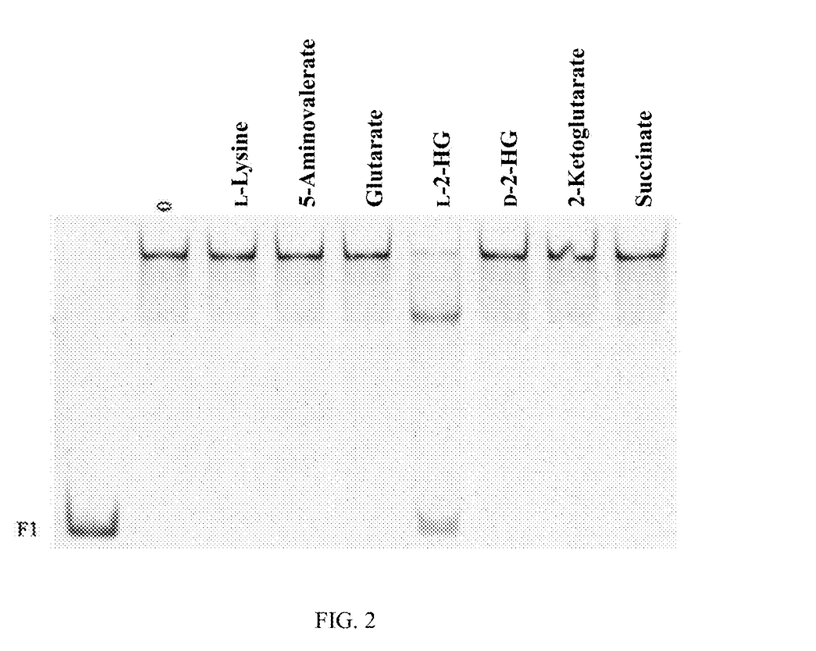
FIG. 2: Specificity analysis of LhgR for L-2-HG.

(2) Electrophoretic Mobility Shift Assays (EMSAs) to Analyze the Effectors of LhgR Using the recombinant plasmid pETDuet-F2-lhgR-F1-lhgO as a template, the promoter region of lhgO (F1) was amplified by PCR using the synthetic primers. The F1 fragment and purified LhgR protein were diluted to 100 nM and 2000 nM using EMSA binding buffer, respectively. 18 μL of EMSA binding buffer containing 60 nM purified LhgR protein and 50 mM of different compounds was incubated for 15 min at 30° C., then 2 μL of F1 fragment at a final concentration of 10 nM was added and incubated for another 30 min at 30° C. 10 μL of the reaction mixture was electrophoresed on a 6% native polyacrylamide gels at 4° C. and 170 volts for approximately 45 minutes, followed by staining with SYBR green I and photographing. As shown in FIG. 2, L-lysine, 5-aminovalerate, glutarate, D-2-HG, 2-ketoglutarate, and succinate could not interfere with the binding of LhgR to DNA fragments, and the shift of DNA bands occurred only in the presence of L-2-HG, indicating that L-2-HG specifically inhibits the binding of LhgR to the lhgO promoter, i.e., LhgR specifically responds to L-2-HG.

The lhgO promoter region of *Pseudomonas putida* W619 was amplified by PCR with the following primer design.

```
Upstream primer:
5'-TACCCAGAGCTTGCTGCGAC-3';

Downstream primer:
5'-GCAGGGGTACCTTGTGATTCTT-3'.
```

Wherein, the LB medium formulation described in step (1) above was: peptone 10 g/L; yeast extract 5 g/L; NaCl 10 g/L, pH 7.0; sterilized at 121° C. for 20 minutes.

The EMSA binding buffer formulation described in step (2) above was: 10 mM Tris-HCl, 50 mM KCl, 0.5 mM EDTA, 10% glycerol, and 1 mM dithiothreitol, adjusted to pH 7.4. The electrophoresis buffer formulation was: 89 mM Tris, 89 mM boric acid, 2 mM EDTA, adjusted to pH 8.3.

Example 2: Construction of L-2-HG Biosensors (1) Construction of L-2-HG Biosensor $LHGFR_{ONOC}$ The gene encoding cyan fluorescent protein mTFP and the gene encoding yellow fluorescent protein Venus were synthesized by General Biosystem Co., Ltd (Anhui), inserted in pETDuet-1 plasmid, and preserved in *Escherichia coli* Top10 strain. Recombinant plasmid pETDuet-mTFP from *E. coli* Top10-pETDuet-mTFP strain and recombinant plasmid pETDuet-Venus from *E. coli* Top10-pETDuet-Venus strain were extracted, respectively. mTFP gene and Venus gene were amplified by PCR using the synthetic primers. The mTFP fragment and pETDuet-1 plasmid were digested by using BamHI/SacI restriction sites, ligated by using T4 DNA ligase to obtain recombinant plasmid pETDuet-mTFP'. Recombinant plasmid pETDuet-mTFP-Venus was obtained by insertion of the Venus fragment into the pETDuet-mTFP' plasmid by using SalI/NotI restriction sites.

Figure 3:
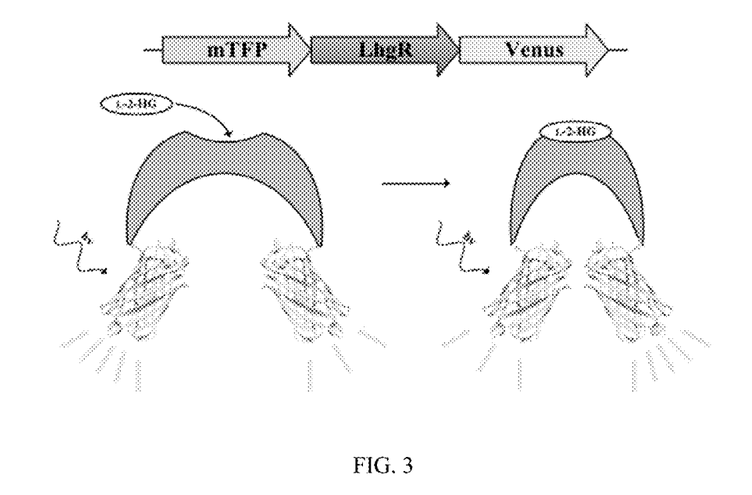
FIG. 3: Schematic diagram of the principle of L-2-HG biosensor.

Recombinant plasmid pETDuet-F2-lhgR-F1-lhgO was used as a template to PCR amplify the full length of the lhgR gene using synthetic primers and inserted into pETDuet-mTFP-Venus using a T5 exonuclease DNA assembly (TEDA) method. That is, the recombinant plasmid pETDuet-mTFP-Venus was linearized using SalI/NotI restriction sites, followed by the addition of 5 μL of lhgR fragment and the linearized recombinant plasmid above into a 15 μL ligation system, where the molar ratio of fragment to plasmid was 4:1. Recombinant plasmid pETDuet-$LHGFR_{ONOC}$ was obtained by incubation at 30° C. for 40 min, followed by 10 min on ice. The recombinant plasmid was named L-2-HG biosensor $LHGFR_{ONOC}$ with a gene sequence length of 2148 bases and its nucleotide sequence is shown in SEQ ID NO. 2. The recombinant plasmids were transformed into *E. coli* DH5α for preservation. The sensor schematic is shown in FIG. 3.

The mTFP gene was amplified by PCR with the following primer design.

```
Upstream primer:
5'-AATTGGATCCGATGGTGAGCAAGGGCGAGGAGA-3',
carrying a BamHI site.

Downstream primer:
5'-AATTGAGCTCCTTGTACAGCTCGTCCATGCCGT-3',
carrying a SacI site.
```

The Venus gene was amplified by PCR with the following primer design.

```
Upstream primer:
5'-AATTGTCGACATGGTGAGTAAAGGCGAAGAACTGT-3',
carrying a SalI site.

Downstream primer:
5'-AATTGCGGCCGCTTATTTATACAGTTCATCCAT GCCC-3',
carrying a NotI site.
```

The full-length lhgR gene of *Pseudomonas putida* W619 was amplified by PCR with the following primer design.

```
Upstream primer:
5'-CGAGCTGTACAAGGAGCTCATGCTAGAACTCCAGCGCCC-3'.

Downstream primer:
5'-CTTTACTCACCATGTCGACGTGCAGGTAGTTCTA-3'.
```

(2) Optimization of L-2-HG Biosensor

The present application achieves optimization of the biosensor by truncating the N-terminal and C-terminal amino acids of the signal recognition element LhgR in the L-2-HG biosensor, i.e., using the recombinant plasmid pETDuet-F2-lhgR-F1-lhgO as a template, PCR amplifying the truncated lhgR gene using synthetic primers, inserting into pETDuet-mTFP-Venus using a T5 exonuclease DNA assembly (TEDA) method, and resulting in a series of L-2-HG biosensor mutants. Dynamic change for L-2-HG was used as an index to screen excellent sensor variants. Among them, the mutants of LhgR$_{ON3C}$ (truncated by three amino acids at the C-terminus of LhgR) and LhgR$_{ON7C}$ (truncated by seven amino acids at the C-terminus of LhgR) have the best dynamic changes for L-2-HG, and the corresponding recombinant plasmids are pETDuet-LHGFR$_{ON3C}$ and pETDuet-LHGFR$_{ON7C}$.

The recombinant plasmid pETDuet-LHGFR$_{ON3C}$ with three amino acids truncated at the C-terminus of LhgR was obtained and named L-2-HG biosensor LHGFR$_{ON3C}$ with a gene sequence length of 2139 bases and nucleotide sequence as in SEQ ID NO. 3.

The recombinant plasmid pETDuet-LHGFR$_{ON7C}$ with seven amino acids truncated at the C-terminus of LhgR was obtained and named L-2-HG biosensor LHGFR$_{ON7C}$ with a gene sequence length of 2127 bases and nucleotide sequence as in SEQ ID NO. 4. The recombinant plasmids were transformed into *E. coli* DH5a for preservation.

The lhgR gene with a C-terminal truncation of three amino acids was amplified by PCR with the following primer design.

```
Upstream primer:
5'-CGAGCTGTACAAGGAGCTCATGCTAGAACTCCAGCGCCC-3'.

Downstream primer:
5'-CTTTACTCACCATGTCGACAGGTAGTTCTATTTTCAGGC-3'.
```

The lhgR gene with a C-terminal truncation of seven amino acids was amplified by PCR with the following primer design.

```
Upstream primer:
5'-CGAGCTGTACAAGGAGCTCATGCTAGAACTCCAGCGCCC-3'.

Downstream primer:
5'-CTTTACTCACCATGTCGACTTTCAGGCGTTTGGCAGAGG-3'.
```

Wherein, the formulation of the 15 μL ligation system in the T5 exonuclease DNA assembly (TEDA) method described in steps (1) to (2) above was: 4 μL 5× isothermal reaction buffer (0.5 M Tris-HCl, 0.05 M MgCl$_2$, 0.05 M dithiothreitol), 0.004 μL 10 U/μL T5 exonuclease, and 11 μL ddH$_2$O.

Example 3: The Response of L-2-HG Biosensor for L-2-HG (1) Expression and Purification of L-2-HG Biosensor The biosensor expression plasmids pETDuet-LHGFR$_{ON0C}$, pETDuet-LHGFR$_{ON3C}$, and pETDuet-LHGFR$_{ON7C}$ described in Example 2 were transformed into the expression strains *E. coli* BL21(DE3) to obtain *E. coli* BL21(DE3)-pETDuet-LHGFR$_{ON0C}$, *E. coli* BL21(DE3)-pETDuet-LHGFR$_{ON3C}$, and *E. coli* BL21(DE3)-pETDuet-LHGFR$_{ON7C}$, respectively, and then screened on LB plates containing ampicillin resistance. Single colonies were picked and verified by PCR, then inoculated in 1 L of LB medium containing ampicillin resistance and incubated at 37° C. and 180 rpm until OD$_{600\ nm}$ about 0.6. 1 mM IPTG was added and protein expression was induced overnight at 16° C. and 160 rpm. LHGFR$_{ON0C}$, LHGFR$_{ON3C}$, and LHGFR$_{ON7C}$ proteins were obtained after isolation and purification.

(2) Detection of Dose-Response Curves of L-2-HG Biosensor for L-2-HG

The purified L-2-HG biosensor protein was diluted to 1 μM using 50 mM Tris-HCl (pH 7.4), and a gradient concentration of L-2-HG was prepared using 50 mM Tris-HCl (pH 7.4). The purified L-2-HG biosensor was mixed with L-2-HG solution in a 3:1 volume ratio under light-proof conditions. 100 μL of the mixture was transferred to a black flat-bottomed 96-well plate, and the fluorescence emission intensity of mTFP and Venus was detected by using an EnSight microplate reader (PerkinElmer, USA). The instrument parameters were set to excitation wavelength of 430 nm and emission wavelengths of 485 nm (mTFP) and 528 nm (Venus), respectively. The background fluorescence intensity without L-2-HG biosensor was subtracted at each emission wavelength, and the ratio of the corrected fluorescence intensity at 528 nm to the fluorescence intensity at 485 nm was used to plot a dose-response curve against the concentration of L-2-HG.

Figure 4:
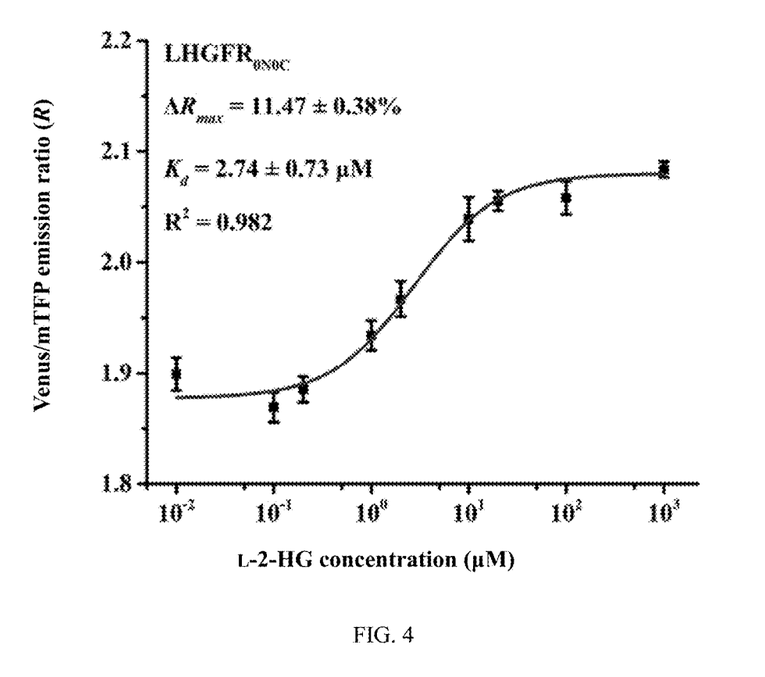
FIG. 4: Dose-response curve of $LHGFR_{ON0C}$ for L-2-HG.
Figure 5:
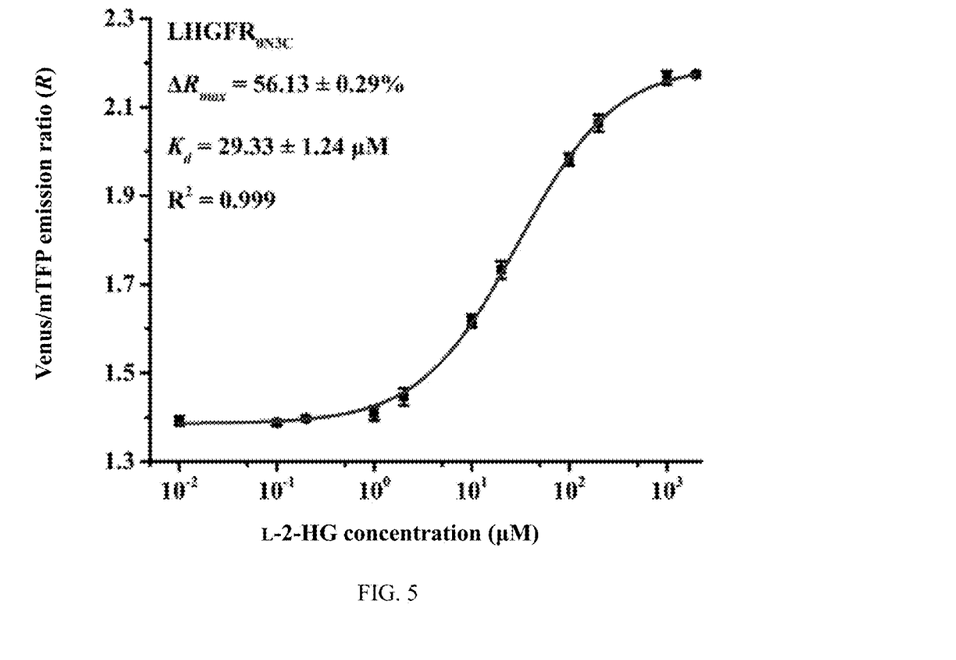
FIG. 5: Dose-response curve of $LHGFR_{ON3C}$ for L-2-HG.
Figure 6:
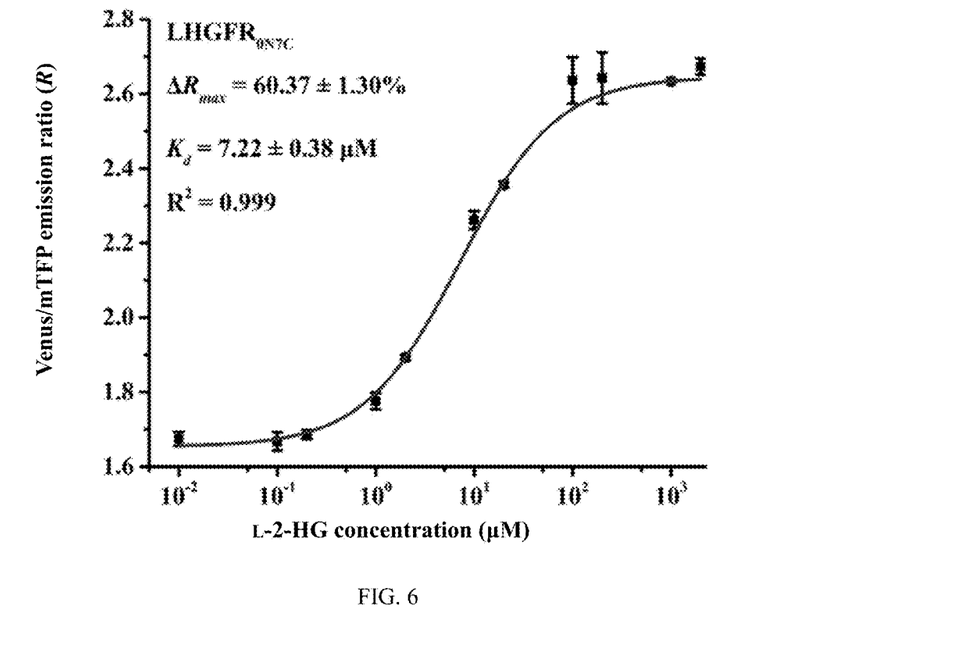
FIG. 6: Dose-response curve of $LHGFR_{ON7C}$ for L-2-HG.

As shown in FIG. 4-6, L-2-HG increased the emission ratio of Venus to mTFP in a dose-dependent manner, the maximum fluorescence ratio changes ($\Delta R_{max}$) of LHGFR$_{ON0C}$ and optimized variants LHGFR$_{ON3C}$ and LHGFR$_{ON7C}$ for L-2-HG were determined to be 11.47±0.38%, 56.13±0.29%, and 60.37±1.30%, respectively, indicating a significant increase in the fluorescence emission ratio in response to the addition of L-2-HG; in addition, the apparent dissociation constants ($K_d$) of LHGFR$_{ON3C}$ and LHGFR$_{ON7C}$ for L-2-HG were 29.33±1.24 μM and 7.22±0.38 μM, respectively, indicating their different affinities for L-2-HG, which can be applied to the detection of different ranges of L-2-HG concentrations.

Figure 7:
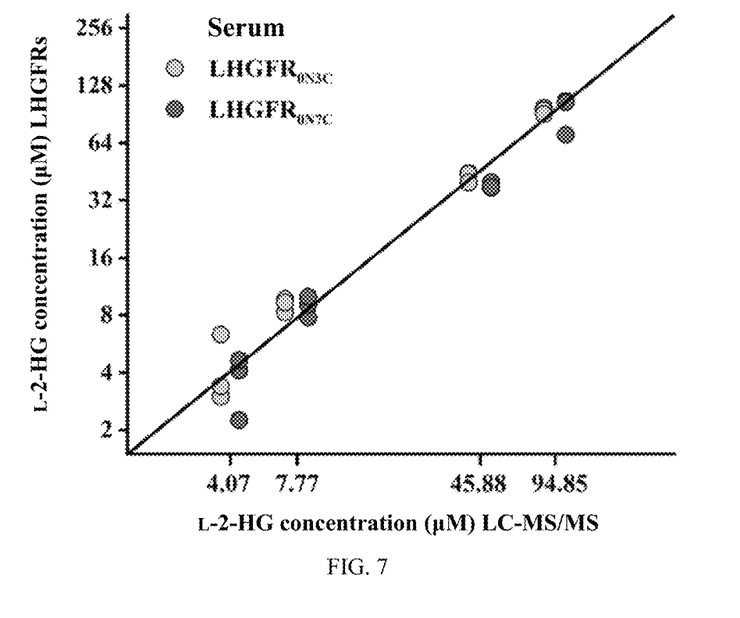
FIG. 7: Comparison between the quantitative results of L-2-HG added in serum by L-2-HG biosensor and LC-MS/MS.
Figure 8:
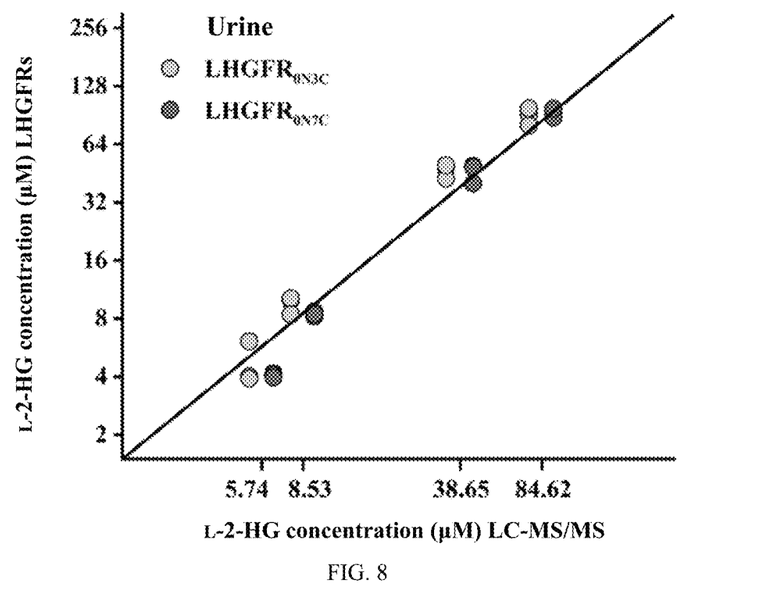
FIG. 8: Comparison between the quantitative results of L-2-HG added in urine by L-2-HG biosensor and LC-MS/MS.
Figure 9:
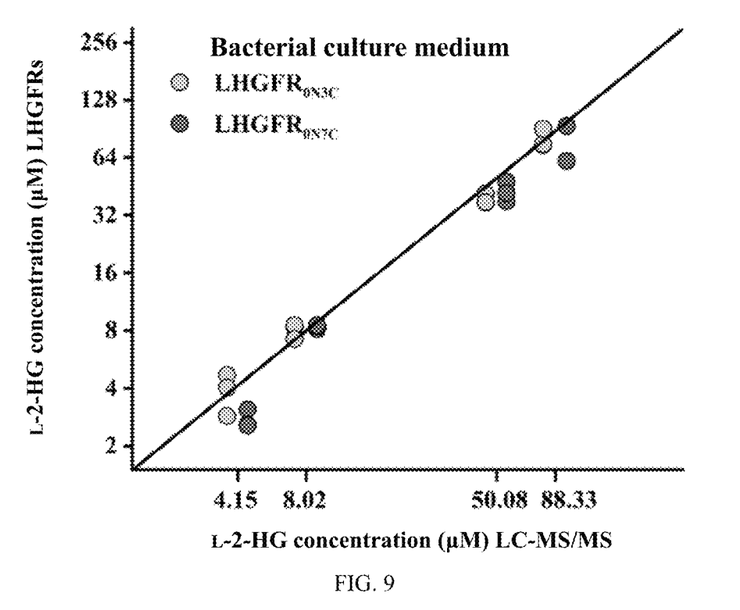
FIG. 9: Comparison between the quantitative results of L-2-HG added in bacterial culture medium by L-2-HG biosensor and LC-MS/MS.

Example 4: Application of L-2-HG Biosensor in the Detection of Biological Samples containing L-2-HG The purified LHGFR$_{ON3C}$ and LHGFR$_{ON7C}$ proteins in Example 3 were diluted to 1 μM by 50 mM Tris-HCl (pH 7.4), and a gradient concentration L-2-HG solution was prepared using the serum and urine of a healthy adult and bacteria culture medium. Purified biosensor was mixed with L-2-HG solution in a 3:1 volume ratio under light-proof conditions. The fluorescence emission intensities of mTFP and Venus were detected by using an EnSight microplate reader (PerkinElmer, USA), and the background fluorescence intensity without L-2-HG biosensor was subtracted at each emission wavelength to obtain dose-response curves and quantitative results for L-2-HG in different biological samples. As shown in FIG. 7-9, L-2-HG could increase the emission ratios of biosensor in a dose-dependent manner. In addition, nearly identical results of L-2-HG quantification were also obtained by either using LHGFR$_{ON3C}$, LHGFR$_{ON7C}$, or using LC-MS/MS, indicating the applicabilities of both biosensors in in vitro L-2-HG quantification of various biological samples.

Example 5: Application of L-2-HG Biosensor for Real-Time Detection of Intracellular L-2-HG concentration in bacteria The *E. coli* BL21(DE3)-pETDuet-LHGFR$_{ON3C}$ strain constructed in Example 3 was inoculated in 50 mL of LB medium containing ampicillin resistance and incubated at 37° C. with 180 rpm to an OD$_{600\ nm}$ of approximately 0.6. Then, 1 mM IPTG was added, and LHGFR$_{ON3C}$ expression was induced at 16° C. with 160 rpm overnight. The bacteria were collected by centrifugation at 6000 rpm for 10 min, washed three times, resuspended in inorganic salt medium without carbon source, and incubated at 37° C. and 180 rpm for 8 h. Endogenous L-2-HG was removed under carbon starvation conditions. 90 μL of carbon starvation-treated bacteria suspensions were mixed with 10 μL of gradient concentrations of L-2-HG in a black flat-bottomed 96-well plate. The fluorescence intensity was detected continuously by using an EnSight microplate reader (PerkinElmer, USA). The instrument parameters were set to excitation wavelength of 430 nm, emission wavelength of 485 nm (mTFP) and 528 nm (Venus), temperature of 37° C., speed of 180 rpm, and detection interval of 5 min. The fluorescence intensity of *E. coli* BL21 (DE3) not expressing L-2-HG biosensor was deducted at each emission wavelength, and the time course curve was plotted as the ratio of the corrected fluorescence intensity at 528 nm to the fluorescence intensity at 485 nm.

Figure 10:
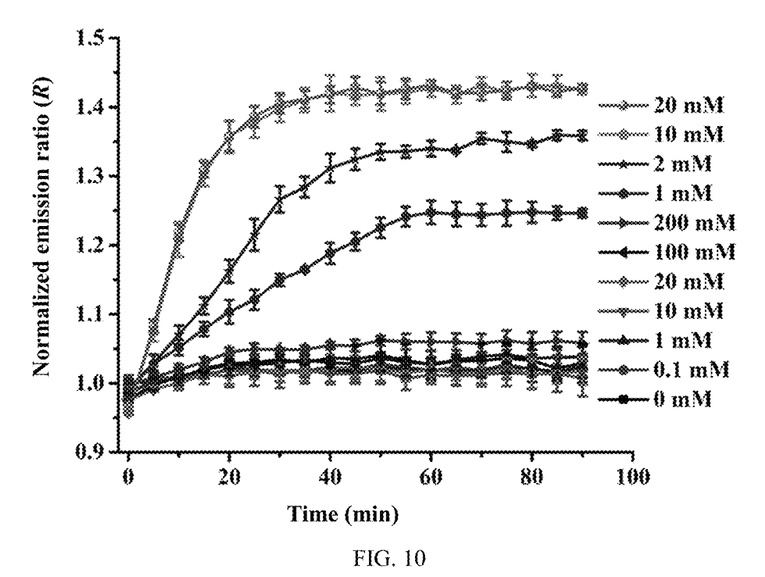
FIG. 10: Real-time monitoring of bacterial intracellular L-2-HG dynamics by $LHGFR_{ON3C}$.

The results are shown in FIG. 10. The results indicate that $LHGFR_{0N3C}$ is able to detect dynamic changes in intracellular L-2-HG concentration of bacteria in real time, and the fluorescence emission ratio of the L-2-HG biosensor increases in response to the addition of L-2-HG, and there is a positive correlation between the level of fluorescence emission ratio change and the concentration of L-2-HG.

In particular, the above inorganic salt medium without carbon source (1 L) was formulated as 1 g $NH_4Cl$, 2.26 g $KH_2PO_4$, 4.1 g $K_2HPO_4$, 2.24 g $NaH_2PO_4 \cdot H_2O$, 3.34 g $Na_2HPO_4$, 10 mL metal ion mixture, pH adjusted to 7.0 by NaOH, and sterilized at 121° C. 20 min. Metal ion mixture (1 L): 14.8 g $MgSO_4 \cdot 7H_2O$, 550 mg $FeSO_4 \cdot 7H_2O$, 45 mg $MnSO_4 \cdot 4H_2O$, 200 μL $H_2SO_4$.

Example 6: Application of L-2-HG Biosensor in the Detection of Intracellular L-2-HG Concentration in Human Cells The nucleotide sequences of $LHGFR_{0N3C}$ and $LHGFR_{0N7C}$ were optimized for mammalian codons and synthesized by General Biosystem Co., Ltd (Anhui). The kozark sequence, 5'-GCCACC-3', was added before the start codon and ligated to pcDNA3.1(+) plasmid and preserved in *Escherichia coli* Top10 strain. The recombinant plasmids pcDNA3.1-$LHGFR_{0N3C}$ and pcDNA3.1-$LHGFR_{0N7C}$ were extracted and transfected into HEK293FT cells, respectively. HEK293FT cells expressing $LHGFR_{0N3C}$ and $LHGFR_{0N7C}$ were trypsinized 48 h following transfection and suspended in 1× Hank's balanced salt solution supplemented with 20 mM HEPES, respectively. Digitonin at a concentration of 10 μM was used to induce cell permeabilization and deplete intracellular L-2-HG. In a black flat-bottomed 96-well plate, 90 μL of the treated cell suspension was mixed with 10 μL of gradient concentration of L-2-HG and the fluorescence intensity was read in a SpectraMax i3 fluorescence plate reader (Molecular Devices, USA). The instrument parameters were set to an excitation wavelength of 430 nm, emission wavelengths of 485 nm (mTFP) and 528 nm (Venus), respectively, and temperature of 37° C. The fluorescence intensity of HEK293FT cells not expressing the L-2-HG biosensor was subtracted at each emission wavelength and the dose-response curve in human cells was plotted as the ratio of the corrected fluorescence intensity at 528 nm to the fluorescence intensity at 485 nm.

Figure 11:
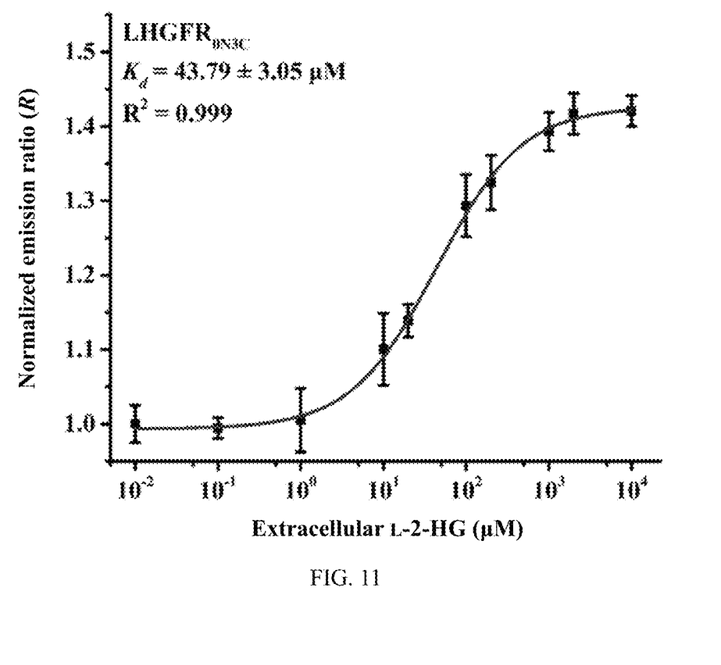
FIG. 11: The detection of L-2-HG levels in human cells by $LHGFR_{ON3C}$.
Figure 12:
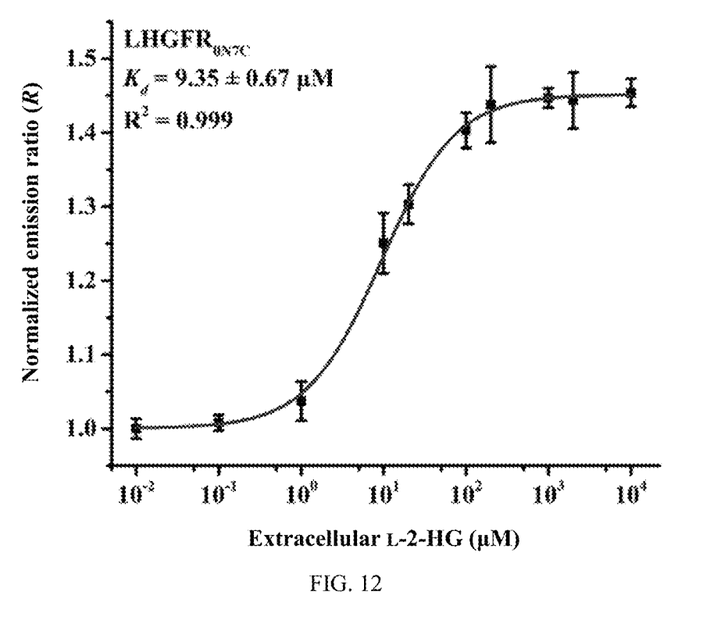
FIG. 12: The detection of L-2-HG levels in human cells by $LHGFR_{ON7C}$.

As shown in FIG. 11-12, $LHGFR_{0N3C}$ and $LHGFR_{0N7C}$ are able to detect intracellular L-2-HG concentration in human cells, and the fluorescence emission ratio of the L-2-HG biosensor increases in response to the addition of L-2-HG.

The foregoing descriptions are only preferred embodiments of the application and are not intended to limit the application. Although the application has been described in detail with reference to the foregoing embodiments, for those skilled in the art, modifications to technical solutions recorded in the foregoing embodiments or equivalent replacement of some of the technical features may still be made. Any modification, equivalent replacement, or improvement made within the spirit and principle of the present application shall fall within the protection scope of the present application

What is claimed is:

1. An L-2-hydroxyglutarate (L-2-HG) biosensor that is a fusion protein comprising:
   a cyan fluorescent protein mTFP,
   an L-2-HG-specific transcriptional regulator LhgR encoded by the nucleotide sequence shown in SEQ ID NO: 1, and
   a yellow fluorescent protein Venus;
   wherein:
   the L-2-HG biosensor is a fusion protein encoded by a recombinant plasmid selected from the group consisting of $LHGFR_{ON0C}$, $LHGFR_{ON3C}$, and $LHGFR_{ON7C}$, wherein:
   the nucleotide sequence of $LHGFR_{ON0C}$ is shown in SEQ ID NO: 2,
   the nucleotide sequence of $LHGFR_{ON3C}$ is shown in SEQ ID NO: 3, and
   the nucleotide sequence of $LHGFR_{ON7C}$ is shown in SEQ ID NO: 4; and wherein:
   binding of L-2-HG to the L-2-HG biosensor induces a conformational change that alters the emission intensity ratio between the fluorescent proteins, wherein the emission intensity ratio increases with increasing concentration of L-2-HG.

2. A method for constructing the L-2-HG biosensor of claim 1, the method comprising:
   (1) synthesizing genes encoding the cyan fluorescent protein mTFP and yellow fluorescent protein Venus, performing PCR amplification using the synthesized genes as templates, and sequentially cloning into pETDuet-1 plasmid through restriction sites BamHI and SacI, and restriction sites Sal and Not, respectively, to construct a recombinant plasmid pETDuet-mTFP-Venus;
   (2) synthesizing a gene encoding transcriptional regulator LhgR in *Pseudomonas putida* W619, performing PCR amplification using the synthesized gene as a template, and inserting into plasmid pETDuet-mTFP-Venus through restriction sites SacI/SalI to obtain a recombinant plasmid pETDuet-$LHGFR_{ON0C}$, designated as $LHGFR_{ON0C}$;
   (3) to improve the sensitivity of the L-2-HG biosensor for L-2-HG detection, performing PCR amplification of combination of the N-terminal and C-terminal truncated amino acids of LhgR, inserting obtained truncated fragments into pETDuet-mTFP-Venus through restriction sites SacI/SalI, and after construction and screening, obtaining either (a) a recombinant plasmid pETDuet-$LHGFR_{ON3C}$ with three amino acids truncated at the C-terminus of LhgR, designated as $LHGFR_{ON3C}$, or (b) a recombinant plasmid pETDuet-$LHGFR_{ON7C}$ with seven amino acids truncated at the C-terminus of LhgR, designated as $LHGFR_{ON7C}$.

3. A method for detecting L-2-HG in biological samples using the L-2-HG biosensor of claim 1, the method comprising:
   preparing gradient solutions of L-2-HG using healthy adult serum, urine, or bacterial culture medium;
   mixing the gradient solutions of L-2-HG with the L-2-HG biosensor in a volume ratio of 1:3 under light-proof conditions;
   measuring fluorescence emission intensities of mTFP and Venus using a fluorescence microplate reader;
   subtracting background fluorescence intensity without the L-2-HG biosensor at each emission wavelength; and
   obtaining a dose-response curve for L-2-HG in the biological samples and quantifying L-2-HG,
   wherein:
   the L-2-HG biosensor responds to increasing L-2-HG concentration in serum, urine, or bacterial culture medium with a dose-dependent increase in fluorescence emission intensity ratio, and
   measurement results of L-2-HG in biological samples by the L-2-HG biosensor are consistent with those determined by liquid chromatography-tandem mass spectrometry (LC-MS/MS) technology.

4. A method for real-time detection of intracellular L-2-HG concentration in bacteria using the L-2-HG biosensor of claim 1, the method comprising:
   introducing L-2-HG biosensor-encoding plasmid pETDuet-$LHGFR_{ON3C}$ into expression strain *E. coli* BL21 (DE3);
   culturing the strain with shaking and inducing $LHGFR_{ON3C}$ expression overnight by adding IPTG;
   subjecting the culture to carbon starvation for 8 hours in a carbon-free inorganic salt medium to clear intracellular L-2-HG;
   mixing 90 L of the carbon-starved bacterial suspension with 10 L of gradient concentrations of L-2-HG solution; and
   continuously measuring fluorescence emission intensities and ratios of mTFP and Venus at 5-minute intervals using a fluorescence microplate reader, wherein the fluorescence emission ratio increases in response to addition of L-2-HG, and the level of change in fluorescence emission ratio is positively correlated with the concentration of L-2-HG, which can be used as an indicator to achieve real-time detection of dynamic changes in intracellular L-2-HG concentration in bacteria.

5. A method for detection of intracellular L-2-HG concentration in human cells using the L-2-HG biosensor of claim 1, the method comprising:
optimizing the nucleotide sequences of $LHGFR_{ON3C}$ and $LHGFR_{ON7C}$ for mammalian codon usage and synthesizing the full-length genes;
adding a Kozak sequence, 5'-GCCACC-3', before the start codon;
ligating the optimized sequences into pcDNA3.1(+) plasmid to obtain recombinant plasmids pcDNA3.1-$LHGFR_{ON3C}$ and pcDNA3.1-$LHGFR_{ON7C}$;
transfecting the recombinant plasmids separately into HEK293FT cells;
after 48 hours, digesting the cells with trypsin and resuspending in 1× Hank's balanced salt buffer supplemented with 20 mM HEPES;
treating cells with 10 µM digitonin to permeabilize them;
mixing 90 µL of the treated cell suspension with 10 µL of gradient concentrations of L-2-HG; and
measuring fluorescence emission intensities and ratios of mTFP and Venus using a fluorescence microplate reader,
wherein:
$LHGFR_{ON3C}$ and $LHGFR_{ON7C}$ are capable of detecting intracellular L-2-HG concentration in human cells, and
the fluorescence emission ratio of the L-2-HG biosensor increases in response to the addition of L-2-HG.

* * * * *